(12) United States Patent
Ritz et al.

(10) Patent No.: US 8,932,663 B2
(45) Date of Patent: Jan. 13, 2015

(54) PYROCARBON COATED BONE IMPLANTS

(71) Applicant: Ascension Orthopedics, Inc., Austin, TX (US)

(72) Inventors: Joseph P. Ritz, Austin, TX (US); Clive Scott, Leander, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 0 days.

(21) Appl. No.: 13/770,640

(22) Filed: Feb. 19, 2013

(65) Prior Publication Data

US 2013/0304226 A1    Nov. 14, 2013

Related U.S. Application Data

(63) Continuation of application No. PCT/US2011/047869, filed on Aug. 16, 2011.

(60) Provisional application No. 61/374,838, filed on Aug. 18, 2010.

(51) Int. Cl.
*A61F 2/28* (2006.01)
*B05D 3/10* (2006.01)
(Continued)

(52) U.S. Cl.
CPC ....... *A61L 27/08* (2013.01); *A61F 2002/30299* (2013.01); *A61L 2430/02* (2013.01); *A61F 2310/00544* (2013.01); *A61F 2002/30163* (2013.01); *A61F 2310/00407* (2013.01); *A61F 2310/00574* (2013.01); *A61F 2/30767* (2013.01); *A61F 2230/0028* (2013.01); *A61L 27/303* (2013.01); *A61F 2002/4248* (2013.01); *A61F 2/4003* (2013.01); *A61F 2310/00497* (2013.01); *A61F 2310/0055* (2013.01);
(Continued)

(58) Field of Classification Search
CPC .... A61L 27/08; A61L 2/30767; A61L 2/4003
USPC .............. 427/2.26, 249.1, 402, 404; 623/23.6
See application file for complete search history.

(56) References Cited

U.S. PATENT DOCUMENTS 5,677,061 A    10/1997   Ely
6,410,087 B1 *  6/2002   Wilde et al. ................ 427/249.1
(Continued)

FOREIGN PATENT DOCUMENTS

WO    WO 2011081797 A1 *  7/2011
WO    WO 2012/024266        2/2012

*Primary Examiner* — Cachet Sellman
(74) *Attorney, Agent, or Firm* — Jenkins, Wilson, Taylor & Hunt, P.A.

(57) ABSTRACT

Methods for forming bone implants for the repair of the ends of bones at orthopedic joints, which implants have a Young's modulus close to that of human cortical bone. Substrates of dense isotropic graphite are coated overall with hard, microporous, isotropic pyrocarbon of specific character such that it can be polished to serve as an articular surface and can also securely receive an anchoring first metal layer through PVD. The first layer has a character such that, by thermal spraying a second biocompatible metal layer thereupon, fusion occurs and thereby anchors an outermost layer that is formed with a network of randomly interconnected pores and a surface character of peaks and valleys designed to promote enhanced appositional growth of cortical bone at the interface therewith.

15 Claims, 3 Drawing Sheets

(51) Int. Cl.
  *C23C 16/00* (2006.01)
  *A61L 27/08* (2006.01)
  *A61L 27/30* (2006.01)
  *A61F 2/40* (2006.01)
  *A61F 2/30* (2006.01)
  *A61F 2/42* (2006.01)

(52) U.S. Cl.
  CPC ............... *A61F2002/3098* (2013.01); *A61F 2002/30769* (2013.01); *A61F 2/4241* (2013.01); *A61F 2230/0093* (2013.01); *A61F 2/3094* (2013.01); *A61F 2310/00491* (2013.01); *A61L 27/306* (2013.01); *A61F 2002/30929* (2013.01); *A61F 2002/4251* (2013.01); *A61F 2310/00485* (2013.01); *A61F 2310/00173* (2013.01)
  USPC ... 427/2.26; 427/2.24; 427/248.1; 427/249.1; 427/402; 427/404; 623/23.5

(56) References Cited

U.S. PATENT DOCUMENTS

| | | | |
|---|---|---|---|
| 2004/0068320 A1* | 4/2004 | Robie et al. | 623/17.16 |
| 2005/0246032 A1* | 11/2005 | Bokros et al. | 623/23.6 |
| 2007/0156249 A1* | 7/2007 | Lawrynowicz et al. | 623/23.51 |
| 2011/0130844 A1* | 6/2011 | Ratron et al. | 623/23.42 |

* cited by examiner

PYROCARBON COATED BONE IMPLANTS

CROSS-REFERENCE TO RELATED APPLICATIONS

This application is a continuation of and claims priority to PCT application No. PCT/US20131/047869 filed Aug. 16, 2011, which claims the benefit of the filing date of U.S. Provisional Patent Application No. 61/374,838 filed Aug. 18, 2010, the disclosures of which applications are hereby incorporated herein by reference.

FIELD OF THE INVENTION

This invention relates to the field of orthopedic bone implants made of artificial materials. More particularly, it relates to bone implants made of pyrocarbon-coated substrates having a modulus similar to that of human bone which, when implanted, have a pyrocarbon articular region and have another region that interfaces with the recipient bone and that is formed so as to promote attachment to such bone without the need for ancillary cement or the like.

BACKGROUND OF THE INVENTION

Orthopedic implants for repair of fractured and/or diseased bones presently constitute a major industrial development because of their ability to rehabilitate patient's joints and load-bearing bone members. Many present-day bone implants utilize biologically compatible metal substrates, typically stainless steel, cobalt-chrome alloys or titanium alloys, and others use ceramic substrates which are nonmetallic inorganic materials often in the form of oxides, nitrides, borides, carbide or sulfides. However, such metal and ceramic implants have a modulus far different from that of human bone. It has now been found that there are long-term advantages to the implantation of prostheses having a modulus of elasticity, i.e. Young's modulus, that is closely similar to that of human cortical bone, particularly where an articular surface is involved at a bone joint. The Young's modulus of cortical bone is measured at between about 20 and 27 GigaPascals. Over the past decade or so, there has been increased interest in producing bone implants of pyrocarbon-coated graphite in order to more closely mimic the mechanical properties of human bone. Cortical bone is a dense, solid mass with only microscopic channels; it forms the outer wall of all bones and is largely responsible for the supportive and protective function of the skeleton. Cortical bone has a Young's modulus of about 20 to 30 Giga Pascal (GPa); such can be closely matched by pyrocarbon that has been coated upon graphite substrates. It has been found that in such instances, long-term compatibility is significantly aided by essentially matching the Young's modulus of a bone implant to that of the cortical bone in which it will be implanted and with which it will interface. As such, artificial isotropic graphite coated with dense isotropic unalloyed pyrocarbon has been found to provide an excellent material for the manufacture of such bone prostheses from the standpoint of its biocompatibility and strength and because it can be deposited with a Young's modulus close to that of cortical bone.

A dense surface layer of pyrocarbon can be deposited by a fluidized bed deposition process so as to exhibit wear-resistant, biocompatible, non-thrombogenic properties and a desired Young's modulus. Such pyrocarbon, upon polishing, provides an excellent articular surface for an implant at a bone joint or the like where there will be articulation with native bone and cartilage. Favorable chemical properties of such pyrocarbon, in addition to its matching mechanical properties, creates an excellent articular surface when included as a part of an implant for a bone that is being repaired. However, in those locations on the implant where it juxtaposes with native bone, the inherent characteristics of the pyrocarbon that render it a desirable articular surface may not result in strong joinder to living bone into which it is being implanted.

Orthopedic manufacturers have searched for biocompatible coatings that will improve long-term attachment of metal and ceramic prostheses and have often coated with ceramics, such as hydroxylapatite, and/or with more biocompatible metals, achieving some improvements but less than total satisfaction. However, the unique nature of such pyrocarbon, an essentially organic material, i.e. organic chemistry being the chemistry of carbon, is such that techniques applicable to coating such hard and/or brittle surface do not translate to the coating of a pyrocarbon surface having this desired Young's modulus. Thus, the search has continued for improved coating procedures that can be used to securely anchor and create a coating upon a particular region of a bone implant that has an overall dense pyrocarbon outer surface in order to significantly enhance its secure attachment to living cortical bone at the locations where there will be interfacial contact.

SUMMARY OF THE INVENTION

A substrate formed of a structurally strong material, such as dense isotropic graphite, is coated overall with a layer of dense microporous isotropic pyrocarbon that has a Young's modulus close to that of human bone in order to create a bone implant or prosthesis that is well-suited for repair of a fractured or diseased bone at a joint where an articular surface is involved. Designated portions of such a pyrocarbon-coated substrate that will interface with the recipient cortical bone into which implantation will occur are then coated (while masking at least the articular surface portion) to provide those designated locations with surface characteristics that will enhance strong, long-term joinder to abutting bone surfaces.

Initially, a thin first or anchor layer of a metal is deposited by physical vapor deposition (PVD) under vacuum conditions onto at least the region or regions of the implant that will interface with human cortical bone. This anchor layer is deposited in such a manner that it penetrates into the interstices of the microporous pyrocarbon and anchors itself thereto while also smoothing the surface of that underlying pyrocarbon in the region or regions upon which such PVD coating is directed and restricted. This thin metal layer, as a result of the penetration into the microporous pyrocarbon creates a strong anchor, and its restricted thickness contributes to the secure, subsequent attachment thereto of a second biocompatible metal layer that is thermal-sprayed so as to have a textured or structured surface. Either the same metal is applied in this plasma-spraying step, or a different biocompatible metal is used having a melting point such that fusion of the two layers will occur. Because the first metal layer is thin, it will locally melt during the subsequent plasma-spraying step, and there will be fusion of it together with globules of plasma-melted metal particles that impact the designated surface as a part of a plasma-spray or other thermal-spray step in an inert gas atmosphere, assuring that a strong bond is created between the two layers. Plasma-spraying is preferably carried out under conditions which create a surface texture having such a defined character and roughness that, upon implantation, a strong, long-term durable, interconnection will result at the interface with living cortical bone being repaired.

In one particular aspect, there is provided a method of making a bone implant, which method comprises the steps of: creating a substrate of structurally strong isotropic graphite of the shape desired for a bone implant, coating the substrate with a surface layer of microporous isotropic pyrocarbon of a density between about 1.7 and 2.1 g/cm$^3$ and a hardness of at least about 200 DPH, which layer has an average thickness of at least about 100 microns and has an average surface roughness ($R_a$) of at least 2 microns, said surface being formed of aggregate carbon particles having an average size of about 0.15 to 0.5 micron and adjacent void regions of an average size of about 0.05 to 0.10 micron, which void regions are present in an amount to create an overall surface porosity of about 2 to 10%, using physical vapor deposition (PVD) to coat a first metal layer at least about 2 microns and not greater than about 10 microns thick atop a designated portion of said isotropic pyrocarbon layer while leaving a portion of said pyrocarbon layer uncoated, said coating being applied by PVD from a vapor atmosphere so that such first metal layer penetrates into said microporous pyrocarbon to create a secure bond and presents an exterior surface smoother than said underlying pyrocarbon surface, and thermal-spraying a second layer of a biocompatible metal onto at least a designated portion of said first metal layer using a device that melts fine metal particles to produce minute molten globules at least having liquefied outer surfaces to thereby provide an outermost, textured, second metal layer having an average thickness of at least about 25 microns and a texture that enhances attachment of said outermost metal surface to cortical bone, said metal of said first layer and said metal of said second layer having melting points within about 200° C. of each other so that said thermal-sprayed particles fuse to said first metal layer.

In another particular aspect, there is provided a bone implant, which comprises: a substrate of structurally strong isotropic graphite, an overall uniform microporous layer of isotropic pyrocarbon having an average thickness of at least about 100 microns which envelops said substrate, which pyrocarbon has a density between about 1.7 and 2.1 g/cm$^3$, a surface roughness not greater than about 3.5 microns, and a Young's modulus of about 20 to 27 GPa, a first layer of metal between about 2 microns and 10 microns thick disposed atop at least a designated portion of said isotropic pyrocarbon layer, which portion will interface with cortical bone into which implantation will be made, such first metal layer penetrating into the interstices of said microporous pyrocarbon as a result of its deposition from a vapor atmosphere, and an outermost second layer of a biocompatible metal disposed atop said vapor-deposited first metal layer and fused thereto, said outermost, textured, second metal layer having an average thickness of at least about 25 microns and a texture that enhances attachment of said outermost metal surface to cortical bone, said metal of said first layer having a melting point not more than about 200° C. greater than that of said biocompatible metal of said second layer so that said second outermost metal layer is fused to said first metal layer with no apparent interface therebetween.

DETAILED DESCRIPTION OF THE PREFERRED EMBODIMENTS

Figure 1:
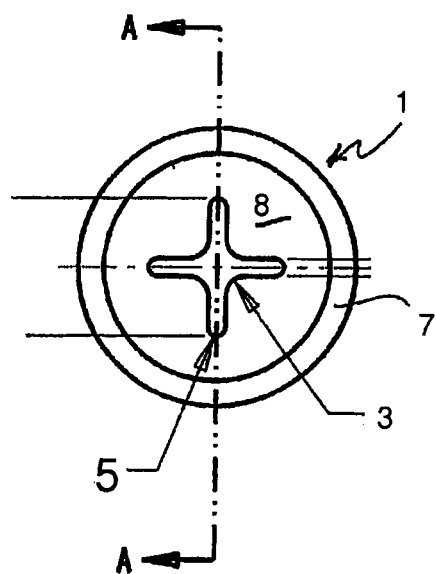
FIG. 1 is a rear view of an implant for resurfacing the humerus.

For the construction of a bone implant having such mechanical properties that mimic the characteristics of cortical bone with which it will interface and with which portions of it will articulate, a graphite substrate is chosen in the form of a dense, isotropic fine grain graphite. A preferred graphite is that commercially marketed as Poco AXF-5Q Biomedical Grade Graphite having a density greater than about 1.75 g/cm$^3$. Such isotropic graphite can be precisely machined to form substrates of desired dimension within close tolerances. As a result, by taking into consideration the thickness of the coating layers that will be subsequently applied, machining is carried out so that the ultimate product will be an implant of desired shape and form requiring only minimal processing, such as polishing of the articular surface.

The carefully machined graphite substrate is encased in an overall pyrocarbon layer or jacket by coating of the graphite substrate in a fluidized bed under conditions that create an external pyrocarbon surface that, when polished, provides an excellent articular surface. It is known that pyrocarbon exhibits many attributes deemed very desirable for a bone implant, including high strength, wear resistance, resistance to cyclic fatigue, biocompatibility, and a modulus of elasticity similar to cortical bone. When polished, the articular surface region provides a low friction surface interface. Pyrocarbon such as that sold under the trademark PYROLITE can be produced with such properties; however, pyrocarbon that is made in accordance with the teaching of U.S. Pat. No. 5,677,061 is particularly preferred. Such unalloyed, dense, substantially pure pyrocarbon is available as On-X™ pyrocarbon.

The machined substrate is coated overall with a substantially uniform layer of microporous isotropic pyrocarbon using a fluidized bed coating apparatus such as that described in U.S. Pat. No. 6,410,087. A mixture of an inert gas, such as nitrogen, argon or helium, and a hydrocarbon such as propane, propylene, methane or the like are caused to undergo pyrolysis in a fluidized bed of small particles wherein the substrate is being levitated. The temperature is generally maintained between about 1300° C. and 1500° C., and coating conditions are monitored so as to produce an isotropic pyrocarbon having a density between about 1.7 and 2.1 g/cm$^3$ and preferably between about 1.8 and about 2.0 g/cm$^3$. The hardness should be at least about 200 DPH, and preferably, the isotrophy is such that the BAF is between about 1.0 and 1.1. The layer deposited should have an average thickness of at least about 100 microns, and the thickness will not normally exceed about 1500 microns. Usually a thickness of about 100-500 microns of isotropic pyrocarbon is deposited.

Coating in such a fluidized bed apparatus produces a coating that can be fairly described as being substantially uniform, it being understood that there are minor increases in thickness at regions where edges of the substrate meet, or where there is a significant change in the geometry of the substrate. The coating conditions are controlled so that the layer has an average surface roughness ($R_a$) of at least about 2 microns and will generally fall within the range of about 2-5 microns. The pyrocarbon deposited is in the form of aggregate carbon particles having an average size of between about 0.15 to 0.5 micron and wherein the adjacent void regions to the these aggregate particles have an average size between about 0.05 and about 0.1 micron. The distribution is such that the void regions are present in an amount such as to create an overall surface porosity of about 2-10%.

The pyrocarbon layer having these characteristics has been found to be particularly suitable for accomplishing dual objectives. This hard carbon can be polished in the region of the articular surface of the bone implant, and when polished to a mirror finish in the presence of a lubricating medium, such as synovial fluid, the surface exhibits very low friction during articulation with human bone or cartilage or with another such polished pyrocarbon surface. At the same time, it has been found that this surface allows designated regions of the substrate, which will include at least those that will interface with cortical bone, to be coated in two stages with a metal coating of a character that promotes strong bone ingrowth so as to ultimately secure the implant excellently to the bone into which it is implanted.

This two-layer exterior coating is created through an initial physical vapor deposition (PVD) step followed by a thermal spraying step. To accomplish such coating, the articular surface is masked to avoid vapor deposition in this region, and then at least a designated region of the bone implant that will be in contact with cortical bone is metal-coated. Optionally, the entire remainder of the substrate, except for the articular surface, can be coated; however, regions that will not be in contact with bone, and portions or all of the stem of such a bone implant, may also be masked if desired.

The first layer is produced by physical vapor deposition of a suitable metal or metal alloy onto the pyrocarbon so as to securely anchor it thereto and provide a surface that has less overall roughness than the pyrocarbon surface. Examples of metals that may be used, either in elemental or alloy form, include titanium, niobium, tungsten, tantalum, zirconium and molybdenum. Preferably, a single metal is used and is chosen for its compatibility with the layer that will be subsequently applied thereatop. The PVD process chosen can be selected from known processes including ion plating, cathodic arc deposition, electron beam deposition, sputtering or the like where vacuum conditions are employed, as well known in this art. Temperatures are generally in the range of about 250 to 450° C. The application of this first metal layer by such a high vacuum PVD process results in the intrusion of the metal atoms into the 2-10% microporous surface in a manner so as to essentially fill the void spaces in the surface regions and thus at least partially envelop the aggregate carbon particles in the surface region, while overcoating the designated pyrocarbon surface to a desired thickness of between about 2 and 10 microns. The result is one of creation of an extremely secure anchor to a pyrocarbon surface; this anchor layer is in turn used to secure an exterior second layer of a highly biocompatible metal which is formed with surface characteristics that induce appositional bone growth at the regions of cortical bone with which the surface will interface upon implantation in the bone being repaired.

The second biocompatible metal layer is created by a thermal spraying process using a metal which preferably has a melting point (MP) within about 200° C. of the MP of the metal used for the first metal layer. More preferably, the MP of the second metal is not greater than about 200° C. above that of the first. Titanium or an alloy thereof that is at least 88% titanium, e.g. about 88-90% Ti, about 6% Al and about 4% V, is the preferred biocompatible metal for the second outermost layer; titanium has a melting point of about 1460° C. Generally, for purposes of this application, reference to coating with titanium should be understood to refer to substantially pure titanium as well as an alloy containing at least about 88% Ti. Another biocompatible metal that might be used as the second metal is zirconium. Preferably, both the first and second layers are formed of the same metal or metal alloy so that the melting point criterion is inherently met; for example, both may be titanium or both may be zirconium. However, when titanium is chosen to be the second layer, then palladium, platinum, zirconium and chromium, which have melting points within about 200° C. of that of titanium, would be candidates for the first metal layer in a two-layer bone growth-inducing surface for this bone implant.

The thermal spraying process generally uses particles of the chosen metal between about 1 and 100 microns, preferably about 5 to 80 microns, and more preferably about 10 to 50 microns in size; the particles are likely graded within such range. During the coating process, the particles are partially melted and accelerated to high velocities as they are passed through a flame or an arc, preferably creating a plasma. These particles splatter onto the underlying relatively thin surface of the first metal layer; because of the generally similar melting points and the relative thinness of the first metal layer, fusion results creating a strong integral bond between the two surface coatings. Preferably, an arc or plasma spray process is employed that may generate a temperatures about 30,000° F. (16,600° C.) in an oxygen-free atmosphere, for example an inert gas atmosphere of nitrogen, helium or argon, such as to create at least partial melting of the particles and the consequent, resultant fusion. This thermal-sprayed second layer of biocompatible metal, which is deposited upon the designated portion of the first metal layer that will be in contact with cortical bone, is preferably created so as to have an average thickness of at least about 25 microns and a texture that will enhance the subsequent growth of cortical bone onto this surface. The dual-metal coated surface thus assures strong ultimate attachment of the pyrocarbon-coated graphite implant to the bone being repaired.

A plasma spraying process is preferably selected and controlled to produce globular particles of titanium atop the PVD first metal layer, having particle sizes between about 5 and 15 microns, which globular particles generally agglomerate to create aggregate particles between about 15 and 30 microns in size. These porous metal structures have only random pore interconnections. Pore sizes average in the range of about 5-12 microns, with some being large enough to provide for actual cortical bone ingrowth. It is felt that the thermal-sprayed layer should be at least about 10 microns thick; however, it is preferably at least about 15 microns thick and more preferably has a thickness of at least about 25 microns. Most preferably, the outer or second layer has an average thickness of about 50 microns to 100 microns. When such a relatively thick, thermal-sprayed layer is deposited at a high temperature, fusion will result at the interface between the layers because of the relative thinness of the vapor-deposited layer, which is chosen to have a lower MP or one not more than 200° C. thereabove. Fusion occurs to such an extent that, even when the same two metals are employed, there is no apparent interface ultimately remaining.

Overall, the pyrocarbon surface is smoothed in those designated regions wherein the vapor-deposited first metal coating is applied, as this metal coating intimately fills the topographic interstices that are present in the isotropic, microporous pyrocarbon layer; however, the important result is that there is an intimate and strong anchor of this first metal layer to the underlying hard pyrocarbon surface. The subsequent plasma-sprayed titanium second layer coating is of greater thickness, and as a result of the melting points of the two metals and the relative thinness of the PVD metal layer, fusion creates an integral structure having no apparent interface. The plasma spray process significantly roughens the surface of the first metal layer, producing a layer of randomly connected pores of, for example, about 10 microns in average diameter, and peaks and valleys on the surface so as to constitute an average surface roughness of about 5 to 10 microns. This surface promotes the appositional growth of cortical bone along with some ingrowth, and the result is a strong attachment between the implant and the bone being repaired. Preferably the average roughness is about 8-10 microns; however, it could be somewhat greater for a thicker second metal coating.

Figure 2:
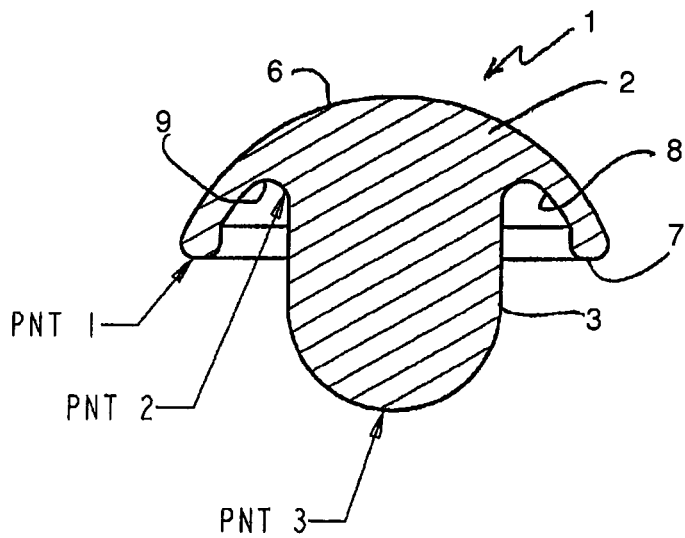
FIG. 2 is an enlarged cross section view of FIG. 1, taken along the line A-A.

FIGS. 1 and 2 show one example of a bone implant that might be made using the method of manufacture set forth hereinbefore in the form of a humeral resurfacing arthroplasty (HRA) 1. The HRA implant 1 comprises a head 2 and a stem 3. The head 2 is generally in the shape of a shell, and the stem 3 is cruciform in shape, comprising four flanges 5 arranged at 90° angles to one another. The head 2 has a convex spherical articular surface 6, which extends to an annular rim 7 that bridges the distance between the spherical outer surface 6 and a concave undersurface 8. Small arcuate junctions 9 interconnect each of the flanges 5 of the stem 3 to the undersurface 8 of the spherical head.

To construct the HRA implant 1, a substrate having a precise desired shape is carefully machined from Poco AXF-5Q biomedical grade graphite. The dimensions are such to allow for the thickness of the coatings to be applied so that the resultant structure requires little or no machining, except for polishing the spherical surface 6 that would constitute the articular region, i.e. where there will be an articulating interface with the patient's glenoid or glenoid replacement. After coating with a substantially uniform layer of chemically pure On-X carbon in a fluidized bed process, as described generally in the '061 patent, the convex spherical surface 6 of the head would be masked. The remainder of the pyrocarbon-coated substrate, which would include the designated area that would interface with cortical bone, is then coated with the first metal layer. In such an instance, the entire undersurface extending from Point 1 of FIG. 2 down to the proximal tip of the stem, i.e. Point 3, would then receive such a coating. Alternatively, because it is within the region from about Point 1 to the inner edge of the annular junctions 9 (Point 2) that will interface with cortical bone, if desired, all or a major portion of the stem 3 might also be masked.

If it is desired to use a titanium first or anchoring layer and a titanium second exterior layer, the masked, pyrocarbon-coated substrate might be subjected to, for example, PVD where it would be exposed to a vapor atmosphere of titanium created by cathodic arc deposition under vacuum conditions. During such a vapor deposition process, metallic titanium atoms would be deposited throughout the interstices of the unmasked, microporous, pyrocarbon coated surface, first filling these irregular microporous surface regions, and then forming an outer surface coating having an average thickness of about 5 microns and a surface roughness ($R_a$) of about 3 microns (which is less than that of the pyrocarbon layer upon which the coating is being deposited). Typical coating times would range between 3 and 6 hours.

Upon completion of the vapor-deposited first anchoring layer of titanium, the still-masked substrate is subjected to plasma-spraying using a chamber filled with an inert atmosphere, e.g. argon, and a plasma spray gun fed with titanium particles of a size between about 10 microns and about 50 microns in an argon stream. The temperature in the region of the arc plasma generator through which the particles are fed would be in the neighborhood of 16,000° C. and would cause the particles to at least partially melt. Plasma spraying is directed against the designated undersurface region of the substrate and results in a porous, globular-like surface across the designated region having pores which are between about 5 and 15 microns in diameter that are randomly interconnected with one another. Multiple passes through the plasma coater may be used, if required, to provide the second, biocompatible, metal coating having an average thickness of about 60 microns.

Following polishing of the convex spherical surface 6 to a mirror finish, testing of the HRA implant shows that the surface 6 exhibits low friction during articulating movement with the glenoid upon implantation. Over a few months time, the two-layer coating strongly remains adhered to the underlying pyrocarbon surface, while significant appositional growth of cortical bone occurs at the locations where there is interfacial contact therewith and effects secure attachment of the implant to the humerus that is being repaired.

Figure 4:
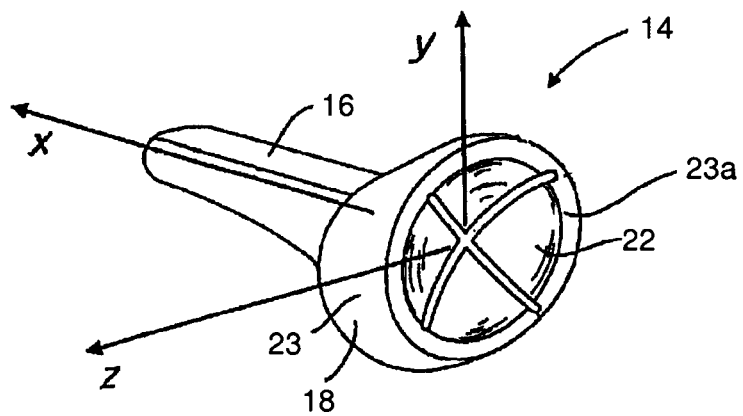
FIG. 4 is a perspective view of the phalangeal element of FIG. 3.
Figure 3:
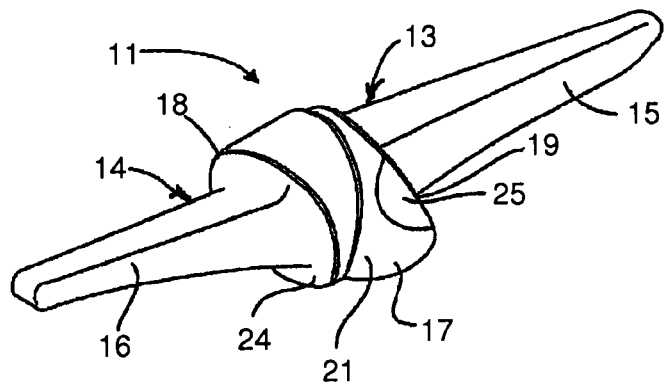
FIG. 3 is a perspective view of an MP prosthetic joint showing the metacarpal element and the phalangeal element in full extension.
Figure 3A:
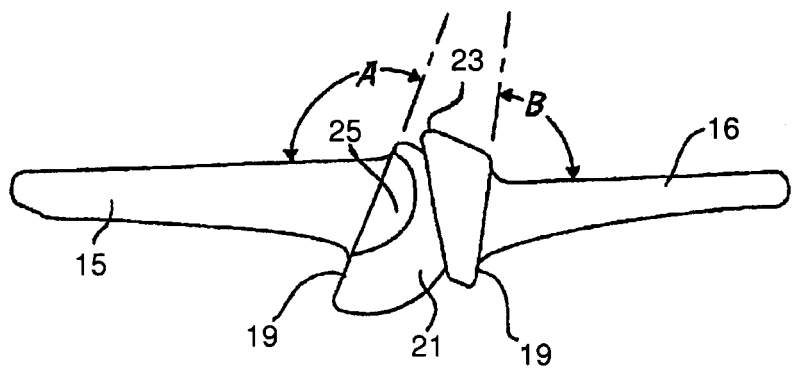
FIG. 3A is a side elevation view of the MP joint of FIG. 3 as viewed from the opposite side.
Figure 5:
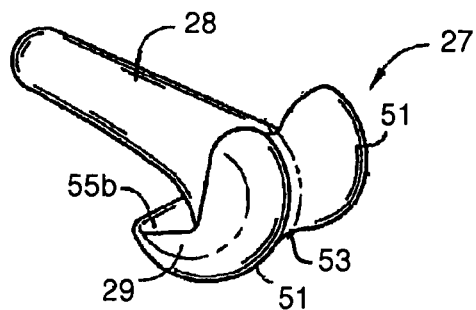
FIG. 5 is a perspective view of a proximal phalangeal element for inclusion as half of a total implant for a prosthetic PIP joint.
Figure 5A:
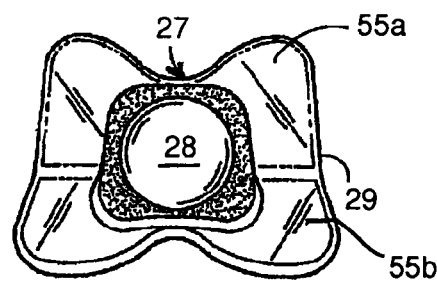
FIG. 5A is a rear view of the proximal phalangeal element of FIG. 5.
Figure 6:
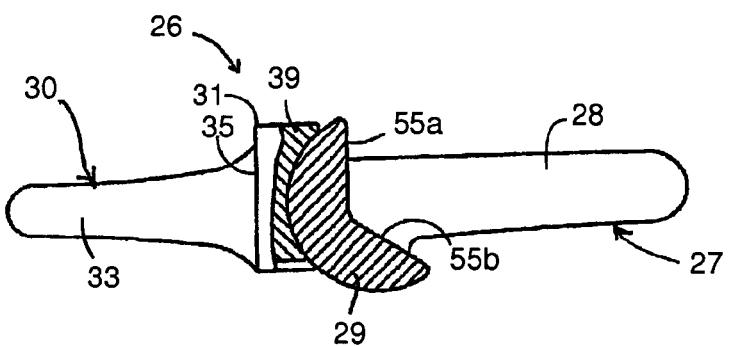
FIG. 6 is a side elevation view, with portions shown in cross section, of a prosthetic PIP joint which includes the proximal phalangeal element of FIG. 5.
Figure 7:
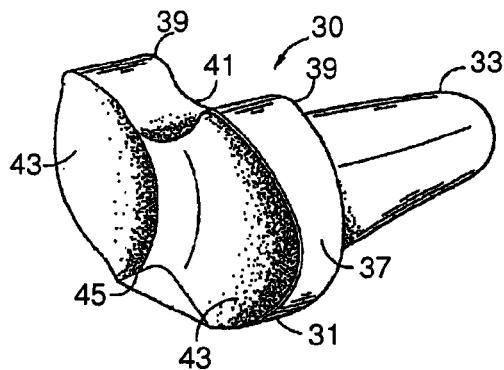
FIG. 7 is a perspective view of the middle phalangeal element shown in FIG. 6.
Figure 8:
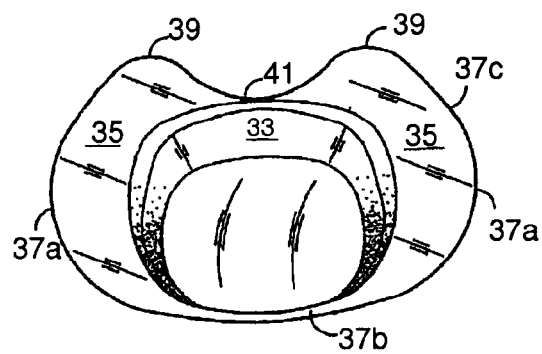
FIG. 8 is a rear view of the element of FIG. 7.

As another example of bone implants that may be made using the aforedescribed process, shown in FIGS. 3, 3A and 4 are elements of a metacarpal phalangeal (MP) replacement joint 11. For this joint prosthesis, a metacarpal element 13 and a phalangeal element 14 are manufactured which have articulating surfaces that form the replacement joint. The metacarpal element 13 has a stem 15 and a head 17, whereas the phalangeal element 14 has a stem 16 and a head 18. The metacarpal element 13 has a convex, generally spherical articular surface 21 and a generally flat rear or undersurface 19 (FIG. 3A) which encircles the stem 15 where it meets the head 17. The head 18 of the phalangeal element 14 has a concave articular surface 22 and a generally flat rear surface 24 which encircles the stem 16 where it meets the head.

To construct this MP joint replacement, substrates having the desired shape are again machined from isotropic graphite and are similarly coated with a layer of pyrocarbon having the aforementioned characteristics having an average thickness of about 150 microns thick. The metacarpal element 13 is then masked so as to cover the convex spherical articular surface of the head 17; from the standpoint of convenience, a pair of flat reliefs 25 formed in the sides of the head 17 would likely also be masked. The designated region for coating of the metacarpal element 13 would be the flat rear surface 19, for it is this surface which will interface with the resected surface of the metacarpus that is being repaired. The stem 15 will be in contact with cancellous bone in the medullary canal region of the metacarpus. The stem is optionally also coated with the two-layer titanium coating, or all or a portion of it may be masked. For example, the end region of the stem 15 distal from the head 17 may be masked if desired. With respect to the phalangeal element 14, at least the concave articular surface 22 would be masked. However, it may be expedient to mask substantially the entire head 18 including the peripheral surface 23 and the rim 23a, except for the designated rear surface 24 where the interface with cortical bone will occur. Likewise, the entire stem 16 may be coated with the two-layer titanium metal coating; however, alternatively, all or a portion of the stem 16 distal from the head 18 may be masked. Once so masked, the phalangeal element 14 and the metacarpal element 13 would be coated as described hereinbefore, and then their concave and convex articular regions would be polished to a mirror finish.

Depicted in FIGS. 5-8 is a prosthesis for replacement of a PIP joint, such as the proximal interphalangeal joint between the proximal phalanx and the middle phalanx. The prosthesis 26 consists of a proximal phalanx implant 27 which has a stem 28 and head 29 and a middle phalanx implant 30. The implant 27 is designed to be implanted in the proximal phalanx for which it would replace the distal end thereof. The middle phalanx implant 30 has a head 31 and a stem 33, and it is designed to replace the proximal end of the middle phalanx. The head 31 has a distal or rear surface 35 that is essentially planar, and the region that surrounds the stem 33 is blended smoothly into the rear surface with billets of small radii. The head 31 is generally formed with a pair of projections 39 which flank a broad central notch 41 (see FIG. 7). The proximal surface 43 of the head is the articular surface, and it is formed with a chamfer 45 in the central region between a pair of concave depressions 43 which receive the proportionally shaped head of the proximal phalanx implant 27. The peripheral surface 37 of the head circumscribes the entire head.

The proximal phalanx implant 27 has a head 29 in the form of a pair of condyles 51 that are separated by a central valley 53. The condyles 51 form the articular surface of which the pair of depressions 43 in the head 31 are portions of mirror images. The rear of the head 29 is in the form of a pair of planar surfaces 55a and 55b which are designed to interface with the resected surface of the proximal phalanx.

In making a PIP joint prosthesis using the method described hereinbefore, graphite substrates are again carefully machined to the desired shape and dimensions taking into consideration the thickness that will be added as a result of the coating operation. For the proximal phalanx implant 27, after coating overall with a layer of pyrocarbon having an average thickness of about 125 microns, the articular surface of the head comprising both condyles 51 and the notch 53 would be masked. The two flat rear surfaces 55a and 55b, which essentially surround the stem 28 where it meets the head 29, would be the primary designated areas for application of the two-metal coating. The stem 28 might optionally also be coated with the two-metal coating. However, the end of the stem distal from the head 29 might be masked, and only the remainder of the stem adjacent the surfaces 55a and 55b may be coated with the two-layer metal coating.

With reference to the middle phalanx implant 30, the two concave depressions which receive the condyles would be masked; however, it might be expedient to mask the entire head including the peripheral surface 37 extending through the notch 41. The designated surface which will primarily interface with cortical bone is the flat rear surface 35, which would be coated with the two-layer metal coating, but all of the stem 33 might also be so coated. Optionally, none of the stem might be coated, or only that region of the stem where it blends smoothly outward to the rear surface might be coated, i.e., with that portion of the stem distal from the head being masked.

Coating of the two isotropic pyrocarbon coated substrates with the two-layer titanium coating, followed by polishing of the articular surfaces to a mirror finish, provides pair of articulating bone implants for a replacement PIP joint which result in a low-friction articular region and which result in strong bonds to the proximal phalanx and the middle phalanx as a result of bony cortical appositional growth into the surface regions. The ability to produce implants having a Young's modulus close to that of human cortical bone and having surfaces which interface with cortical bone and enhance bony appositional growth results in a superior PIP joint that is wear-resistant and well-received in the patient's finger.

Although the invention has been described in such detail as to provide the best mode of construction as presently envisioned by the inventors, it should be understood that various modifications and changes as would be obvious to one having ordinary skill in this art may be made without departing from the scope of the invention which is defined in the claims appended hereto. Although the invention has been illustrated with regard to the production of certain exemplary bone implants, it should be understood that the use of the invention is not so restricted. A wide variety of bone implants where there will be an articular surface on the head of the implant which is held in place by a protruding stem of an appropriate form and shape may advantageously be produced using this method.

Particular features of the invention are emphasized in the claims which follow.

The invention claimed is:

1. A method of making a bone implant, which method comprises the steps of:
    creating a substrate of structurally strong isotropic graphite of the shape desired for a bone implant,
    coating the substrate with a surface layer of microporous isotropic pyrocarbon of a density between about 1.7 and 2.1 g/cm$^3$ and a hardness of at least about 200 DPH, which layer has an average thickness of at least about 100 microns and has an average surface roughness ($R_a$) of at least 2 microns, said surface being formed of aggregate carbon particles having an average size of about 0.15 to 0.5 micron and adjacent void regions of an average size of about 0.05 to 0.10 micron, which void regions are present in an amount to create an overall surface porosity of about 2 to 10%,
    using physical vapor deposition (PVD) to coat a first metal layer at least about 2 microns and not greater than about 10 microns thick atop a designated portion of said isotropic pyrocarbon layer while leaving a portion of said pyrocarbon layer uncoated, said coating being applied by PVD from a vapor atmosphere so that such first metal layer penetrates into said microporous pyrocarbon to create a secure bond and presents an exterior surface smoother than said underlying pyrocarbon surface, and
    thermal-spraying a second layer of a biocompatible metal onto at least a designated portion of said first metal layer using a device that melts fine metal particles to produce minute molten globules at least having liquefied outer surfaces to thereby provide an outermost, textured, second metal layer having an average thickness of at least about 25 microns and a texture that enhances attachment of said outermost metal surface to cortical bone, said metal of said first layer and said metal of said second layer having melting points within about 200° C. of each other so that said thermal-sprayed particles fuse to said first metal layer.

2. The method of claim 1 wherein said implant substrate includes a stem and a head which has an articular surface that is masked to remain uncoated during said PVD step.

3. The method of claim 2 wherein said head articular surface is a convex spheroidal articular surface.

4. The method of claim 3 wherein said head also has a concave spheroidal surface which surface generally surrounds one end of said stem and wherein said designated portion comprises said concave surface.

5. The method of any one of claims 1-3 wherein said isotropic pyrolytic carbon coating is created by deposition in a fluidized bed at a temperature of 1300 to 1500° C.

6. The method of claim 5 wherein said isotropic pyrocarbon has a BAF between about 1.0 and about 1.1 and a Young's modulus of about 20 to 27 GPa.

7. The method of claim 6 wherein said first metal layer is titanium which is deposited to have an average thickness of about 2 to 5 microns.

8. The method according to claim 7 wherein said second metal layer is titanium having an average thickness between about 50 microns and 100 microns.

9. The method of any one of claims 1-3 wherein said biocompatible metal deposited as said second metal layer is titanium.

10. The method of claim 9 wherein said titanium second metal layer is deposited onto said vapor-deposited first metal layer using a plasma spray process.

11. The method of claim 10 wherein said resultant plasma-sprayed layer of titanium contains single particles between about 5 and 10 microns in size.

12. The method of claim 10 wherein said plasma-sprayed layer of titanium has resultant aggregate particles between about 10 and 30 microns in size.

13. The method of claim 10 wherein said plasma-spraying employs particles of titanium of a size between about 10 microns and 50 microns.

14. The method according to claim 10 wherein said plasma-spraying is carried out to deposit a textured coating having an average thickness of about 50 microns to about 100 microns.

15. The method according to claim 14 wherein said textured titanium coating has a surface roughness of between about 5 microns and about 10 microns.

* * * * *